United States Patent [19]

El-Sayad et al.

[11] Patent Number: 4,491,665
[45] Date of Patent: Jan. 1, 1985

[54] METHOD OF PREPARING ISOMERS OF BIS ISOQUINOLINIUM COMPOUNDS

[75] Inventors: Hassan A. El-Sayad, Chapel Hill; Roy A. Swaringen, Jr., Durham; David A. Yeowell, Chapel Hill, all of N.C.

[73] Assignee: Burroughs Wellcome Co., Research Triangle Park, N.C.

[21] Appl. No.: 253,299

[22] Filed: Apr. 13, 1981

Related U.S. Application Data

[63] Continuation-in-part of Ser. No. 182,446, Jul. 29, 1980, abandoned, which is a continuation-in-part of Ser. No. 86,530, Oct. 19, 1979, abandoned.

[51] Int. Cl.³ .................... C07D 401/10; A61K 31/47
[52] U.S. Cl. .................................. 546/140; 424/258; 546/147
[58] Field of Search ........................ 546/140

[56] References Cited

U.S. PATENT DOCUMENTS

| | | | |
|---|---|---|---|
| 3,004,031 | 10/1961 | Taylor et al. | 546/140 |
| 4,179,507 | 12/1979 | Stenlake et al. | 546/140 |
| 4,192,877 | 5/1980 | Savarese et al. | 546/140 |
| 4,235,906 | 11/1980 | Savarese et al. | 546/140 |

Primary Examiner—Glennon H. Hollrah
Assistant Examiner—James H. Turnipseed
Attorney, Agent, or Firm—Donald Brown

[57] ABSTRACT

This invention provides the neuromuscular blocking agents of formula (I):

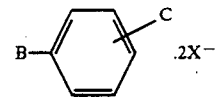

where B and C are each a group of formula (II) and are meta or para to one another:

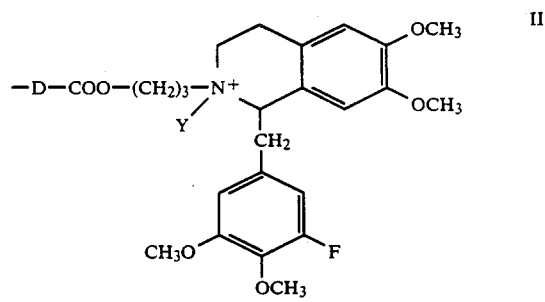

wherein D is $CH_2CH_2$ or $CH=CH$ (preferably trans); Y is alkyl of 1-4 carbon atoms (methyl, ethyl, propyl or butyl); E and F and H or $OCH_3$; $X^-$ is an anion, preferably pharmaceutically acceptable; and the substituted benzyl and substituted propyl groups are in a trans relationship relative to each other in the nitrogen-containing ring.

Methods for preparing the compounds, pharmaceutical formulations containing the compounds, and their use are also described.

1 Claim, No Drawings

METHOD OF PREPARING ISOMERS OF BIS ISOQUINOLINIUM COMPOUNDS

This is a continuation-in-part of application Ser. No. 182,446 filed July 29, 1980 which is now abandoned and is a continuation-in-part of application Ser. No. 86,530 filed Oct. 19, 1979 which is also now abandoned.

BACKGROUND OF THE DISCLOSURE

In anesthesia, neuromuscular blocking agents are used to provide skeletal muscular relaxation during surgery and during intubation of the trachea.

In general there are two types of neuromuscular blocking agents in use, non-depolarizing and depolarizing.

The non-depolarizing agents include d-tubocurarine, pancuronium, gallamine, diallyltoxiferine and toxiferine.

The depolarizing agents include succinylcholine and decamethonium. All of the conventional non-depolarizing agents when used for producing skeletal muscle relaxation in surgery have a long duration of action, e.g. 60 to 180 minutes in man. The depolarizing agents, on the other hand, provide muscle relaxation with duration of action shorter than that of the non-depolarizing agents.

For example, succinylcholine provides a short duration of action of about 5 to 15 minutes whereas decamethonium provides about 20 to 40 minutes duration of muscle relaxation in man.

The long duration of action of non-depolarizing agents is unacceptable in many surgical procedures which take less than one hour because the patient is not generally fully recovered from their effects e.g., the patient may be unable to breathe adequately on his or her own.

Each non-depolarizing agent has inherent side effects. For example, gallamine and pancuronium may cause tachycardia, and d-tubocurarine and diallyltoxiferine may cause hypotension.

While these drugs can be pharmacologically antagonized with anticholinesterase agents, this obviously necesssitates the administration of a second drug which itself may have its own side effects, e.g., bradycardia, gut spasm and bronchorrhea. Thus, to overcome the aforementioned side effects of the anticholinesterase agents, a third drug, an anticholinergic drug, e.g. atropine must also be given.

The depolarizing agents to the best of applicants' knowledge have no pharmacologic antagonists. While in most cases there is no need to reverse the effects of the depolarizing agents, in certain patients the effects of succinylcholine are much prolonged because of abnormal metabolism of the agent by the patient.

The depolarizing agents due to that mode of action which initially causes skeletal muscle contraction and stimulation of smooth muscles are also known to cause the following side effects in certain instances: increased intraocular, and intragastric tension, cardiac arrhythmias, potassium release, and muscle pain.

These side effects caused by the depolarizing agents are not caused by the non-depolarizing agents. It is, therefore, clearly evident that a new neuromuscular blocking agent is needed which would combine the short duration of action of the depolarizing agents with the relatively few side effects and the reversibility of the non-depolarizing agents.

It should be understood that while non-depolarizing agents generally have few side effects, gallamine and pancuronium may cause tachycardia and d-tubocurarine and diallyltoxiferine may cause hypotension.

Surprisingly, the compounds of the present invention appear to be free of these side effects at the dosages anticipated being used clinically in tests made to date. Reference may be made to the text:

The Pharmacological Basis of Therapeutics-Fifth Edition, edited by Louis S. Goodman and Alfred Gilman published by The McMillian Co., copyright 1975, Chapter 28, author George B. Koelle, for further description of neuromuscular blocking agents.

Reference should also be made to the following articles:

Neuromuscular Blocking Activity of a New Series of Quaternary N-Substituted Choline Esters—British Journal of Pharmacology, September, 1971, vol, 43, No. 1, p. 107.

The Pharmacology of New Short Acting Non-depolarizing Ester Neuromuscular Blocking Agents: Clinical Implications—published in Anaesthesia and Analgesia . . . Current Researches, Vol. 52, No. 6, p. 982, November–December, 1973.

Potential Clinical Uses of Short-Acting Non-depolarizing Neuromuscular-Blocking Agents as Predicted from Animal Experiments—published in Anaesthesia and Analgesia . . . Current Researches, Vol. 54, No. 5, p. 669, September–October, 1974; and U.S. Pat. No. 3,491,099, for a further description of neuromuscular blocking agents.

British Pat. No. 3004031 granted Oct. 10, 1961 discloses a group of substituted laudanosinium salts having neuromuscular blocking activity with non-depolarizing properties.

Belgium Pat. No. 869,415 granted Jan. 31, 1979 discloses a group of substituted tetrahydroisoquinolinium salts having neuromuscular blocking activity, with non-depolarizing properties and a short duration of action. Spanish Patent of Invention No. 477.257 granted Apr. 25, 1979 [notice published in Spanish Official Gazette of Aug. 1, 1979] discloses a second group of substituted tetrahydroisoquinolinium salts having neuromuscular blocking activity, with non-depolarizing properties and an intermediate duration of action. The compounds disclosed in the above-mentioned patents comprise various mixtures of cis and trans isomers of undefined compositions.

The four asymmetric centers present in each compound in all the above mentioned patents allow for sixteen possible stereoisomers. However, only ten stereoisomers can exist due to the symmetry of the molecular structure; for dl pairs (one all trans, one all cis, two cis, trans) and two meso forms (one all cis, one all trans). It is now recognized that the route of synthesis as well as the actual experimental conditions determines the cis/trans ratio and the stereoisomeric ratio. None of the issued patents addresses the question of the stereoisomers, hence they do not teach or even suggest ways for separating the different isomers. Moreover, the above mentioned patents do not teach or suggest that different potencies, durations of action or side effects would exist for the different isomers in the mixtures.

We have discovered a way of providing the all trans (one dl pair, one meso form) and the all cis (one dl pair, one meso form) compounds. These diastereomers exhibit different neuromuscular blocking activities in their potencies and/or durations of action. In the cat, the all trans compounds showed superior potencies, three to six times that of the corresponding all cis compound and a shorter duration of action. In the monkey, the difference in potencies was not as evident, but the durations of action of the all trans compounds were markedly shorter (2-3 times) of those of the all cis compounds. The unexpected differences in duration were explained by measuring the hydrolysis rates by acetylcholinesterase in vitro. The rates of hydrolysis of the cis compounds were very slow compared to that of the corresponding trans form.

Accordingly, this invention provides new neuromuscular blocking agents (sometimes called muscle relaxants) of the formula (I):

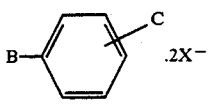

where B and C are each a group of formula (II) and are meta or para to one another:

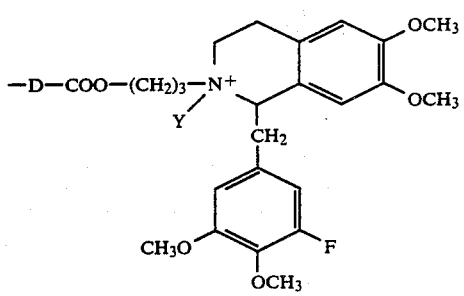

wherein D is $CH_2CH_2$ or $CH=CH$ (preferably trans); Y is alkyl of 1-4 carbon atoms (methyl, ethyl, propyl or butyl); E and F are H or $OCH_3$; $X^-$ is an anion, preferably pharmaceutically acceptable; and the substituted benzyl and substituted propyl groups are in a trans relationship relative to each other in the nitrogen-containing ring.

Preferred compounds are those wherein Y is methyl.

Compounds having particularly good potency combined with a short duration of action are bis{3-[trans-1,2,3,4-tetrahydro-6,7-dimethoxy-N-methyl-1-(3,4,5-trimethoxybenzyl)isoquinolinium]propyl}1,3-phenylenedipropionate salts, particularly as the dichloride, diiodide or ditosylate salts.

Compounds having particularly good potency combined with an intermediate duration of action are bis{3-[trans-1,2,3,4-tetrahydro-6,7-dimethoxy-N-methyl-1-(3,4,5-trimethoxybenzyl)isoquinolinium]propyl}1,4-phenylene-(E,E)-diacrylate and bis{3-[trans-1,2,3,4-tetrahydro-6,7-dimethoxy-N-methyl-1-(3,4,5-trimethoxybenzyl)isoquinolinium]propyl}1,3-phenylene-(E,E)-diacrylate salts, particularly as the dichloride, diiodide or dimesylate salts.

Since the activity of the compounds of the invention resides in the dication, the nature of the anion $X^-$ is relatively unimportant. Suitable pharmaceutically acceptable anions include iodide, mesylate, tosylate, bromide, chloride, sulphate, phosphate, hydrogen phosphate, acetate, benzenesulphonate, succinate, maleate, naphthalenesulphonate and propionate.

It will be appreciated that the compounds of the invention exist as an approximately 1:1 mixture of the racemic (dl) pair and the meso-isomer. This invention further provides means for obtaining the compounds of formula (I) when in the form of one of the aforesaid isomers substantially free of the other isomers, and mixtures of one of the isomers with one or both of the other isomers.

It is preferred that the compounds of the invention be provided in a form where the ratio of the trans, trans compound of the invention to the total of any corresponding cis, cis and cis, trans compounds present as impurities is at least 96:4.

The compounds of formula (I) are used as neuromuscular blocking agents in conjunction with surgery or for intubation of the trachea by conventional parenteral administration, e.g. intramuscular or intravenous administration in solution. The compounds of the present invention shown in formula (I) are administered to patients such as monkeys and man (humans) and other mammals to achieve a neuromuscular block. The dosage for each type of patient will vary because of the peculiarities of the species. However, a suitable intravenous amount or dosage of the compounds of formula (I) to obtain paralyses for monkeys and humans suitable for surgery would be 0.05 to 1.5 mg/kg of body weight, and most preferably 0.1 to 1.0 mg/kg of body weight, the above being based on the weight of the dication which is the active ingredient.

The dosage for intramuscular administration is two to four times the intravenous dose. The compounds of this invention would normally be readministered about every 5 to 45 minutes, depending on whether the activity of the compound is of short or intermediate duration, preferably every 5 to 30 minutes, after initial administration or given as a continuous infusion depending upon the length of time a muscular block is desired, and as determined by the anaesthetists and surgeon in charge of the patient. The compounds of this invention are reversible using conventional anticholinesterase agents such as neostigmine and edrophonium and appear to avoid the side effects associated with the depolarizing agents.

The compounds of formula (I) are therefore useful for producing a short or intermediate duration neuromuscular blockade, and the present invention provides a method of producing such blockade in mammals, e.g. man, or monkeys, by intravenously injecting a dose of 0.05 to 1.5 mg/kg to the mammal.

The compounds may be presented in a pharmaceutical formulation for parenteral administration. The formulation may be an aqueous or non-aqueous solution or emulsion in a pharmaceutically acceptable liquid or mixture of liquids, which may contain bacteriostatic agents, antioxidants, buffers, thickening agents, suspending agents or other pharmaceutically acceptable additives. Such formulations are normally presented in unit dosage forms such as ampoules or disposable injection devices, or in multidose forms such as a bottle from which the appropriate dose may be withdrawn, all such formulations sterile.

The compounds of this invention may be presented as a powder, e.g. as a unit dose in a sealed vial to which sterile water or other pharmaceutically acceptable sterile liquid vehicle may be added, preferably by aseptic techniques.

A suitable unit dose to obtain a neuromuscular block for mammals, e.g. humans or monkeys is about 1.0 mg to 300 mg and most preferably 5.0 to 200 mg.

The compounds of this invention if desired may be administered in conjunction with other non-depolarizing agents such as listed above.

Thus a suitable pharmaceutical parenteral preparation for administration to human will preferably contain 1.0 to 300 mg of the compounds of formula (I) of this invention in solution.

A simple and preferred formulation is a solution of the compound of formula (I) in water which may be prepared by simply dissolving the compound into previously sterilized pure water, i.e. pyrogen free water under aseptic conditions and sterilizing the solution.

The tertiary benzyltetrahydroisoquinoline is quaternized with an appropriate 1,3-dihalopropane, such as 1-bromo-3-chloropropane 3-chloro-1-iodopropane or 3-bromo-1-iodopropane. From the resulting N-alkyl-N-3-halopropyl-1-benzyltetrahydroisoquinolinium halide the trans isomer is separated and is boiled in water with the silver salt of the appropriate dicarboxylic acid, yielding silver halide and the benzyltetrahydroisoquinolinium salt of the acid. This salt reacts to the corresponding ester on heating, preferably at 90° to 140° C. For example, the generalized reaction is illustrated as follows:

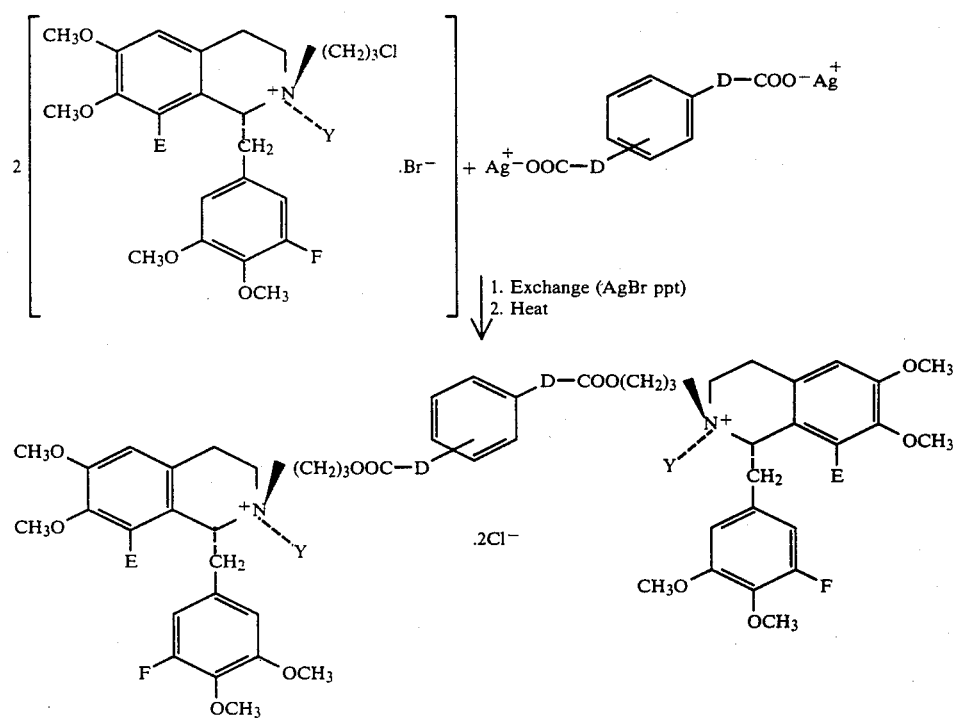

The compound of formula (I) may also be administered as an infusion of a dextrose solution or a saline solution, e.g. Ringers' solution.

The compounds may also be administered in other solvents such as alcohol, polyethylene glycol and dimethylsulphoxide. They may also be administered intramuscularly as a suspension.

The compounds of this invention provide the same percentage neuromuscular block at unexpectedly lower doses than the previously described cis/trans mixtures. Consequently, the possibility of side effects such as abnormal lowering of blood pressure, histamine release, tachycardia, etc. is substantially reduced. Furthermore, our invention provides means to prepare mixtures of specified isomeric composition.

The compounds of formula (I) may be prepared by the following methods, using a substituted tetrahydroisoquinolinium salt having the trans configuration as previously defined.

Method 1

Benzyltetrahydroisoquinolins are prepared in the customary fashion from homoveratrylamine or mescaline and homoveratric acid or 3,4,5-trimethoxyphenylacetic acid via the Bischler-Napieralisky reaction and reduction/alkylation.

where D, Y, E and F are as defined above. The desired salts are then prepared by ion exchange using conventional methods such as metathesis with HX or a silver salt, an anion exchange resin, etc.

Method 2

The appropriate 1-benzyltetrahydroisoquinoline prepared as described in Method 1 is quaternized with a 3-halopropanol such as 3-iodo, 3-bromo, or 3-chloropropanol. This is illustrated below where E, F, X and Y are as defined above.

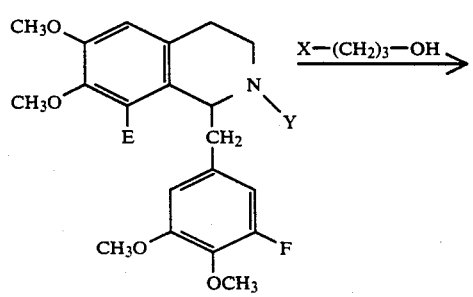

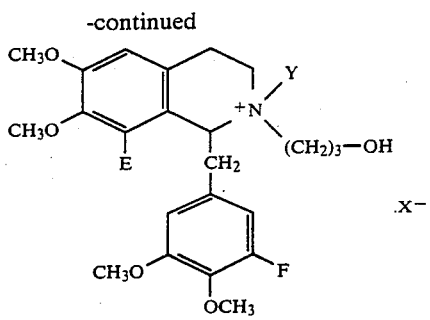

This process may be carried out in a variety of solvents (e.g., acetonitrile, lower alcohols, DMF, water, aromatic hydrocarbons, etc) over temperatures ranging from ambient to reflux. The trans isomer is separated as described below.

The bis acid chloride of an appropriate meta- or para-phenylene dicarboxylic acid is prepared in the usual fashion by treatment with a reagent such as thionyl chloride.

The bis acid chloride is then esterified with, e.g., two moles of the appropriate quaternary salt containing a 3-hydroxypropyl chain. This is illustrated below where D, E, F, X and Y are as defined above.

propyl-5'-methoxylaudanosinium salts, for example, are diastereomers and theoretically separable by physical methods, e.g. crystallization. However, literature precedent suggests that this separation is difficult. For example Stenlake et al. [J. B. Stenlake, W. D. Williams, N. C. Dhar, and I. G. Marshall, Eur. J. Med. Chem.—Chimica Therapeutica, 9, 233 (1974)] reported the synthesis of mixtures of trans and cis N-ethyllaudanosinium iodides but were unable to separate them: "All attempts to separate the components of these mixtures by crystallization and chromatographic techniques were unsuccessful." We examined a variety of solvents for recrystallization of the trans/cis mixtures of N-3-hydroxypropyl-5'-methoxylaudanosinium iodide (trans/cis ratio about 2.5–2.7/1) afforded by quaternization of 5'-methoxylaudanosine with 3-hydroxypropyl iodide (See Table I). Most solvent categories were unsatisfactory. The mixture of trans/cis quaternary iodides was largely insoluble in ethers (tetrahydrofuran, 1,4-dioxane, 1,2-dimethoxyethane), esters (ethyl acetate, ethyl propionate), ketones (acetone, 2-butanone), and aromatic hydrocarbons (benzene, toluene, xylene). The insoluble residues showed little or no enrichment with trans isomer. Solvents useful for the separation included acetonitrile, some chlorinated hydrocarbons (e.g. dichloromethane, 1,2-dichloroethane), some alcohols (e.g. ethanol, 2-propanol), and water. Water is the most preferred

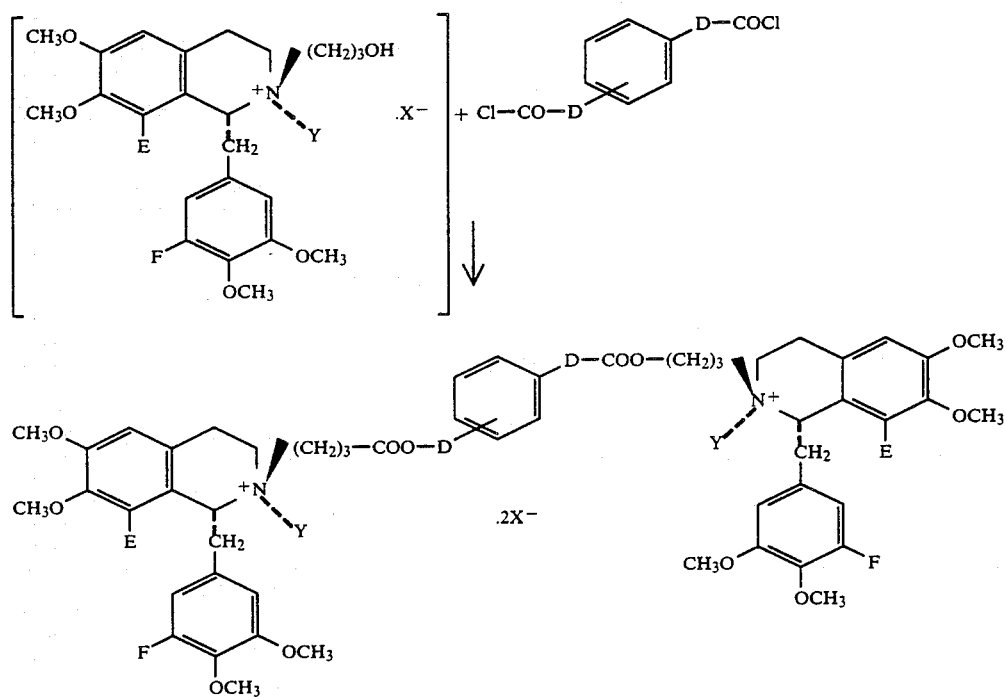

To prepare the all trans bis quaternary salts, having enhanced potencies and greater freedom from side effects, requires the preparation of a trans-N-3-hydroxypropyl-N-alkyltetrahydroisoquinolinium salt with a total of 4–6 methoxy groups as described in formula (II) for coupling with the meta or para-phenylene dipropionic or diacrylic acids. Trans and cis-N-3-hydroxysolvent. Once enrichment of the trans isomer has been accomplished (e.g. by water recrystallization) further recrystallization from a variety of solvents (e.g. acetonitrile, ethanol) or trituration with acetone suffices to raise the trans content to ~98% or higher.

TABLE I

Separation of Trans/Cis N—3-Hydroxypropyl-5'-methoxylaudanosinium Iodide
A sample of trans/cis iodide (2.6/1 by HPLC) was heated in a solvent, filtered hot, cooled to 25° and filtered again.

| Solvent | Concentration (ml/g) | Trans/Cis Ratio (Recovery) Insoluble Salts | Recrystallized Salts |
|---|---|---|---|
| tetrahydrofuran | 10 | 2.7/1 (90%) | NP |
| 1,4-dioxane | 10 | 2.8/1 (71%) | NP |
| 1,2-dimethoxyethane | 10 | 2.6/1 (83%) | NP |
| acetone | 10 | 2.7/1 (81%) | 1.1/1 (1%) |
| 2-butanone | 10 | 3.4/1 (82%) | 1/1.1 (8%) |
| ethyl propionate | 10 | 2.7/1 (96%) | NP |
| ethyl acetate | 10 | 2.6/1 (88%) | NP |
| acetonitrile | 10 | CS | 1/2.6 (28%) |
| dichloromethane | 2 | 1/15.8 (21%) | |
| chloroform | 2 | CS | 1/6.2 (2%) |
| carbon tetrachloride | 10 | 2.6/1 (96%) | NP |
| 1,2-dichloroethane | 5 | 1/1.2 (30%) | 4/1 (58%) |
| nitromethane | 2 | CS | 1/1 (30%) |
| nitroethane | 2 | CS | 2.3/1 (89%) |
| benzene | 10 | 2.7/1 (~100%) | NP |
| toluene | 10 | 2.7/1 (~100%) | NP |
| xylene | 10 | 2.5/1 (~100%) | NP |
| methanol | 2 | CS | 6.8/1 (9%) |
| ethanol | 5 | 9.8/1 (27%) | 1.9/1 (58%) |
| 2-propanol | 5 | 12.7/1 (38%) | 1.5/1 (25%) |
| 2-methoxyethanol | 2 | CS | 2.8/1 (31%) |
| formamide | 2 | CS | NP |
| N,N—dimethylformamide | 2 | CS | NP |
| N—ethylacetamide | 2 | CS | 2.6/1 (96%) |
| Dimethyl sulfoxide | 2 | CS | NP |
| Hexamethylphosphoramide | 2 | CS | NP |
| Water | 6.74 | CS | 1/5.17 (31%) |

Abbreviations: NP = No Precipitate, NA = Not Assayed, CS = Complete Solution

In another approach to the separation of trans/cis quaternary salt mixtures the iodide was first changed to a different anion. The mixture of iodides was converted to the corresponding chlorides by standard methods (anion exchange chromatography, metathesis with silver chloride, and metathesis with HCl gas) and a variety of solvents was examined, for separating the isomers (See Table II). Again, most solvents were unsatisfactory. Among ethers only 1,4-dioxane was selective. Ketones, esters, and aromatic hydrocarbons were ineffective. Nitroalkanes (nitromethane, nitroethane), acetonitrile, some alcohols (especially ethanol and 2-propanol), some chlorinated hydrocarbons (e.g. dichloromethane, 1,2-dichloroethane), dimethylsulfoxide, hexamethylphosphoramide, and N-substituted amides are useful solvents for obtaining the quaternary chloride enriched in the trans isomer. N-substituted amides (e.g. N,N-dimethylformamide, N,N-dimethylacetamide, N-formylpiperidine, N-formylmorpholine, N-methylformamide, N-methylacetamide, and N-ethylacetamide) are preferred solvents for the trans/cis separation. These amides may be used as recrystallization solvents or solvents for slurrying enriched trans mixtures to increase further the trans isomer content.

TABLE II

Separation of Trans/Cis N—3-Hydroxypropyl-5'-methoxylaudanosinium Chloride
A sample of trans/cis iodide (2.9/1 by HPLC) was heated in a solvent, filtered hot, cooled to 25° and filtered again.

| Solvent | Concentration (ml/g) | Trans/Cis Ratio (Recovery) Insoluble Salts | Recrystallized Salts |
|---|---|---|---|
| tetrahydrofuran | 10 | 2.6/1 (97%) | NP |
| 1,4-dioxane | 10 | 132/1 (67%) | 1/6 (24%) |
| 1,2-dimethoxyethane | 10 | 3.3/1 (96%) | NP |
| acetone | 10 | 3/1 (95%) | 1/15 (2%) |
| 2-butanone | 10 | 3.8/1 (97%) | 1/11 (3%) |
| ethyl propionate | 10 | 3.4/1 (99%) | NP |
| ethyl acetate | 10 | 3.3/1 (95%) | NP |
| acetonitrile | 10 | 100/1 (50%) | 8.6/1 (6%) |
| dichloromethane | 10 | 101/1 (36%) | NP |
| chloroform | 2 | CS | NP |
| carbon tetrachloride | 10 | 2.4/1 (99%) | NP |
| 1,2-dichloroethane | 10 | 6/1 (76%) | 1/2.9 (12%) |
| nitromethane | 5 | CS | 9.4/1 (56%) |
| nitroethane | 10 | 80/1 (42%) | NP |
| benzene | 10 | 2.9/1 (99%) | NP |
| toluene | 10 | 3.1/1 (97%) | NP |
| xylene | 10 | 2.4/1 (96%) | NP |
| methanol | 2 | CS | NP |
| ethanol | 5 | CS | 17/1 (32%) |
| 2-propanol | 10 | 69/1 (30%) | 9.1/1 (18%) |
| 2-methoxyethanol | | | |

TABLE II-continued

Separation of Trans/Cis N—3-Hydroxypropyl-5'-methoxylaudanosinium Chloride
A sample of trans/cis iodide (2.9/1 by HPLC) was heated in a solvent, filtered hot, cooled to 25° and filtered again.

| Solvent | Concentration (ml/g) | Trans/Cis Ratio (Recovery) | |
|---|---|---|---|
| | | Insoluble Salts | Recrystallized Salts |
| formamide | 2 | CS | NP |
| N,N—dimethylformamide | 5 | CS | 6.7/1 (54%) |
| N—ethylacetamide | 2 | CS | 8.8/1 (76%) |
| Dimethyl sulfoxide | 2 | CS | 18/1 (34%) |
| Hexamethylphosphoramide | 10 | 67/1 (40%) | NP |
| Water | 2 | CS | NP |

Abbreviations: NP = No Precipitate, NA = Not Assayed, CS = Complete Solution

We have found that a particularly good separation of the trans isomer from the crude cis/trans mixture may be achieved by crystallization of the N-(3-hydroxypropyl)-N-methyl compound in the form of the iodide (cis/trans mixture) from water. The cis-isomer crystallizes preferentially. If required, the trans-enriched filtrate may then be converted to the chloride, for example, by conventional anion exchange chromatography (e.g. using Dowex 1-X8 chloride resin), and the solute recovered and slurried with dimethylformamide, when the cis-isomer preferentially dissolves, to leave a product containing only a trace of the cis-isomer.

We have also separated the trans/cis mixture of N-3-hydroxypropyllaudanosinium iodide; N-3-hydroxypropyl-8-methoxylandanosinium iodide; and N-3-hydroxypropyl-5'-8-dimethoxylaudanosinium iodide by fractional crystallization.

It is desirable to use an intermediate having less than about 2% of the corresponding cis-isomer, in order to obtain a compound of formula (I) containing less than 4% of the cis, cis and cis, trans isomers. This degree of separation may be readily achieved using the processes outlined above.

Method 3

The appropriate 1-benzyltetrahydroisoquinoline prepared as described in Method 1 is quaternized with a 3-halopropanol such as 3-iodo, 3-chloro or 3-bromopropanol, and the trans-N-3-hydroxypropyl-1-benzyltetrahydroisoquinolinium salt is separated from the cis isomer as in Method 2.

The trans quaternary salt is coupled with the appropriate meta- or para-phenylenedipropionic acid by direct esterification. This method may also be used to couple the trans-quaternary salt with meta or para-phenylenediacrylic acid, but this reaction is slower. This operation is carried out in a suitable solvent (e.g. 1,2-dichloroethane) using an acid catalyst (e.g. p-toluenesulfonic acid). The reaction is driven toward comopletion by removal of water by use of drying agents (e.g. molecular sieves) or by azeotropic distillation. Temperatures ranging from ambient to reflux may be employed. The final salt may be changed if desired by conventional anion exchange methods.

As previously stated, the compounds of formula (I) exist in three stereoisomeric forms, which may be separated from each other, if desired, by conventional methods. For example, the meso-isomer may be separated from the (dl)-pair by fractional crystallization, or by preparative HPLC, and the d- and l-isomers may be separated from each other by conversion to a salt of a single isomer of an optically active acid, followed by fractional crystallization. The product may then, if desired, be converted to an alternative salt by conventional anion exchange methods.

m- and p-phenylene diacrylic acids were prepared through Knoevenagel-Doebner condensation of isophthalic and terephthalic aldehydes with malonic acid. Terephthalic aldehyde (150 mM) and malonic acid (180 mM) were mixed with pyridine (45 ml) and piperidine (1.5 ml). The mixture was heated on a steam bath (85°-95°) for 3 hours. The solution was then cooled at room temperature and distilled in vacuum to remove pyridine. The solid residue was washed in hot 2-propanol (70°) to remove residual pyridine. The product, p-phenylene diacrylic acid, was filtered and dried (mp>275°).

m-Phenylene diacrylic acid was prepared from isophthalaldehyde in exactly the same way. (mp>275°).

m- and p-phenylene dipropionic acids may be prepared using conventional processes by catalytic reduction, e.g. by reacting the corresponding phenylene diacrylic salt with hydrogen at 40 to 45 psi gauge pressure in the presence of 5% palladium on charcoal in water or dimethylformamide at room temperature to 55° C. For another method, see also Wagner & Zook, Synthetic Organic Chemistry © 1973, page 431, method 26.

The compounds of this invention may sometimes include water of hydration in various amounts and it is intended that this invention include such compounds containing water of hydration.

The following examples illustrate the invention but are not intended to be limiting. Temperatures are in degrees centigrade (uncorrected).

Primary analysis of the quaternary salt intermediates and the di-quaternary salt final products was accomplished by high performance liquid chromatography (HPLC). Samples dissolved in methanol were injected onto a 25 cm×4 mm silica gel column and eluted with an acidic methanol. Detection was based on absorbance at 280 nm; percentages were derived by integration of the areas under the curves. Nuclear magnetic resonance (NMR) spectra, combustion analyses, and Karl Fischer water analyses were obtained as needed to support structures. The stereochemistry of the cis and trans quaternary salts was confirmed by x-ray crystallography of the cis iodide and the trans perchlorate of N-3-hydroxypropyl-5'-methoxylaudanosinium salts.

EXAMPLE 1

N-3-hydroxypropyl-5'-methoxylaudanosinium iodide (Belgian patent No. 869,415 and West German Offenlegungsschrift No. 2833505) (50 g, 73% trans) was dissolved in 337 mL of hot water. The mixture was cooled to 30° and then stirred at room temperature for 3 hours. The solids were collected by filtration and dried in a vacuum oven (60°/3 hr) to yield 15.5 g of solids analyzed by HPLC as 84% cis. The trans rich filtrate was applied to a 5×60 cm column packed with 110 g of Dowex 1-X8 chloride in water and eluted with 100 mL of water. The eluate was concentrated in vacuo to dryness. The residue was triturated with 40 mL of acetone; the mixture was cooled to 5° and filtered. The solid was vacuum dried (60°/3 hr) to yield 28 g of crude trans chloride. The crude product was slurried in dry DMF (70 mL) at 70°-75° for 15 minutes. The mixture was cooled to 5° and filtered. The solids were washed with cold DMF (15 mL) and refluxed in acetone (100 mL) for 15 minutes. The suspension was cooled to 5° and filtered; the solids were washed with cold acetone and dried in a vacuum oven to yield 24.7 g (80.5%) of trans-N-3-hydroxypropyl-5'-methoxylaudanosinium chloride, mp 209°-211°. HPLC analysis showed this material to be 99.3% trans.

EXAMPLE 2

Crude N-3-hydroxypropyl-5'-methoxylaudanosinium iodide (95.1% pure, 71.9% trans by HPLC, 412 g) was recrystallized from 1348 mL of water. The trans rich mother liquor was chromatographed on 1.00 kg of Dowex 1-X8 chloride. The eluate and washings were combined and concentrated in vacuo to a viscous oil. The residue was triturated with 3000 mL of refluxing acetone. Approximately 2000 mL of acetone were removed by atmospheric distillation. The residual slurry was chilled and filtered to yield 225 g of crude trans chloride (97.7% trans). The crude product was slurried in 2 parts of DMF (w/v) for 30 minutes at 75°. The mixture was cooled to 0° and filtered. The cake was washed with the DMF liquors and then with acetone. Finally the damp product was slurried in 800 mL of refluxing acetone for 15 minutes and then the mixture was cooled, filtered, and dried to yield 206 g (87.0%) of trans-N-3-hydroxypropyl-5'-methoxylaudanosinium chloride (99.9% trans by HPLC).

EXAMPLE 3

N-3-hydroxypropyl-5'-methoxylaudanosinium iodide (50 g, 72.5% trans, 26.7% cis) was dissolved in 337 mL of hot water. The solution was cooled to 25° for 3 hours. The mixture was filtered to yield 15.5 g of cis iodide (83.8% cis—purified (>99% cis) by recrystallization from methanol). The filtrate was concentrated to dryness in vacuo to yield the trans iodide (95.6% trans by HPLC). The crude trans iodide was purified by recrystallization from dry acetonitrile (2.5 mL CH$_3$CN/g) to yield 99.6% trans iodide (71% recovery). In similar experiments 94.5% trans iodide gave 99.3% pure trans (67% recovery) and 97% trans gave 99.6% trans (86% recovery). Trans iodide was also purified by trituration with acetone (3 mL/g): 92.7% trans gave 97.7% trans (95% recovery). Ethanol (95%, 4 mL/g) could also be used as a recrystallization solvent: 97.7% trans gave 99.6% trans (61% recovery).

EXAMPLE 4

Trans-N-3-hydroxypropyl-5'-methoxylaudanosinium chloride (>99% trans by HPLC, 25.7 g) was suspended in 375 mL of 1,2-dichloroethane and 50-75 mL of solvent was distilled off to remove any water present. The mixture was cooled to ~70° and 1,3-phenylenedipropionyl chloride (6 g, prepared by treatment of the corresponding acid with thionyl chloride) was added as a solution in dry 1,2-dichloroethane. The mixture was heated at reflux for 25 minutes; HPLC analysis indicated ~93% of product. The reaction mixture was cooled, stirred over potassium carbonate for 2.5 hours, filtered, and concentrated in vacuo to dryness. The crude product was dissolved in 300 mL of chloroform, and the solution was washed twice with 5% sodium chloride, twice with water, dried over anhydrous sodium sulphate, and concentrated in vacuo to give bis{3-[trans-1,2,3,4-tetrahydro-6,7-dimethoxy-N-methyl-1-(3,4,5-trimethoxybenzyl)isoquinolinium]propyl} 1,3-phenylenedipropionate dichloride as a white amorphous solid, 24 g (87.4% based on a dihydrate).

EXAMPLE 5

Trans-N-3-hydroxypropyl-5'-methoxylaudanosinium chloride (>99% trans by HPLC, 124.6 g) was suspended in 1720 mL of dry 1,2-dichloroethane. The mixture was heated to reflux and 500 mL of solvent was removed by distillation. The mixture was cooled to 50° and a solution of 1,3-phenylenedipropionyl chloride, 32.7 g, in 100 mL of 1,2-dichloroethane was added. The mixture was stirred at reflux for 45 minutes and cooled to 8°. Triethylamine, 22.9 g, was added giving an exotherm to 15°. The mixture was cooled to 10°, stirred for 15 minutes, and concentrated in vacuo. The residue was stored at 5° overnight and then dissolved in 1800 mL of chloroform. The chloroform solution was washed with 5% sodium chloride (2×450 mL), water (2×450 mL), dried over magnesium sulphate, clarified by treatment with charcoal, and concentrated in vacuo until foaming began. The residue was triturated with hexane and the mixture concentrated in vacuo again until foaming began. This process was repeated three times until a solid product was obtained. The slightly oily product was transferred to a mortar and triturated again with hexane to give a granular solid which was collected by filtration and dried (48 hours at 40°) in a vacuum oven to yield 127.5 g (85.3%) of bis{3-[trans-1,2,3,4-tetrahydro-6,7-dimethoxy-N-methyl-1-(3,4,5-trimethoxybenzyl)isoquinolinium]propyl} 1,3-phenylenedipropionate dichloride.

EXAMPLE 6

Trans-N-3-hydroxypropyl-5'-methoxylaudanosinium chloride (>99% trans by HPLC), 5.06 g, was coupled with E,E-1,4-phenylenediacryloyl chloride, 1.27 g, by the procedure of Example 4 to yield 3.0 g (50.7% as a dihydrate) of bis{3-[trans-1,2,3,4-tetrahydro-6,7-dimethoxy-N-methyl-1-(3,4,5-trimethoxybenzyl)isoquinolinium]propyl} 1,4-phenylene-(E,E)-diacrylate dichloride.

EXAMPLE 7

1,3-Phenylenedipropionic acid (0.58 g), trans-N-3-hydroxypropyl-5'-methoxylaudanosinium chloride (3.2 g), p-toluenesulphonic acid monohydrate (1.75 g), and dichloroethane (60 mL) were combined in a 100 mL flask equipped with a sintered glass Soxhlet containing molecular sieve #4. The mixture was heated at reflux and was monitored by HPLC. After 35 hours the reaction mixture was cooled and washed with water (2×50 mL). The dichloroethane layer was stirred overnight with charcoal and magnesium sulphate (anhydrous). The mixture was filtered and evaporated to dryness to give 3.11 g (84%) of bis{3-[trans-1,2,3,4-tetrahydro-6,7-dimethoxy-N-methyl-1-(3,4,5-trimethoxybenzyl)isoquinolinium]propyl} 1,3-phenylenedipropionate ditosylate.

EXAMPLE 8

Trans-N-3-hydroxypropyl-5'-methoxylaudanosinium chloride (5.00 g), 1,3-phenylenediacrylic acid (1.08 g), and p-toluenesulfonic acid monohydrate were combined in 1,2-dichloroethane and reacted by the procedure of Example 7. After 99 hours at reflux HPLC analysis showed 46.7% of bis{3-[trans-1,2,3,4-tetrahydro-6,7-dimethoxy-N-methyl-1-(3,4,5-trimethoxybenzyl)isoquinolinium]propyl} 1,3-phenylene-(E,E)-diacrylate ditosylate.

EXAMPLE 9

Trans-N-3-hydroxypropyl-5'-methoxylaudanosinium chloride (>99% by HPLC), 5.07 g, was coupled with 1,4-phenylenedipropionyl chloride, 1.29 g, to yield 4.7 g (79.6% as dihydrate) of bis{3-[trans-1,2,3,4-tetrahydro-6,7-dimethoxy-N-methyl-1-(3,4,5-trimethoxybenzyl)isoquinolinium]propyl} 1,4-phenylenedipropionate dichloride.

EXAMPLE 10

To a solution of bis{3-[trans-1,2,3,4-tetrahydro-6,7-dimethoxy-N-methyl-1-(3,4,5-trimethoxybenzyl)isoquinolinium]-propyl} 1,3-phenylenedipropionate diiodide tetrahydrate (0.65 g (prepared according to Example 4 using the pure trans iodide of Example 3) in acetonitrile (10 mL) was added to a solution of silver methanesulphonate (0.22 g) in acetonitrile (10 mL). The mixture was stirred for 15 minutes and filtered to remove the precipitate of silver iodide. The filtrate was concentrated in vacuo to a brown oil which was taken up in denatured ethanol (SD3A) and filtered to remove excess silver methanesulphonate. The alcohol was evaporated in vacuo, and the residue was dissolved in acetonitrile and filtered. The acetonitrile was evaporated in vacuo and the residue was dissolved in acetone. The acetone solution was filtered through Celite® (filter aid) and evaporated to dryness to yield 0.40 g (65%) of fluffy yellow crystals of bis{3-[trans-1,2,3,4-tetrahydro-6,7-dimethoxy-N-methyl-1-(3,4,5-trimethoxybenzyl)isoquinolinium]propyl} 1,3-phenylenedipropionate dimethanesulphonate. Calcd. for $C_{62}H_{82}N_2O_{14}.2CH_3O_3S.4H_2O$: C, 57.29; H, 7.21; N, 2.08; S, 4.79 Found: C, 57.37; H, 7.10; N, 2.09; S, 4.79.

EXAMPLE 11

N-3-Hydroxypropyl-5'-methoxylaudanosinium iodide (10 g, 71% trans) was dissolved in methanol (100 mL). The solution was heated to reflux and hydrogen chloride gas bubbled through for 5 hours. The mixture was evaporated in vacuo, and the residue was stored overnight in a dessicator containing sodium hydroxide pellets. Acetone was added and evaporated in vacuo. Denatured alcohol (SD3A) was added and evaporated in vacuo and the process repeated a second time. Upon the addition of acetone and seed crystals there was obtained 4 g of N-3-hydroxypropyl-5'-methoxylaudanosinium chloride (87% trans by HPLC). Slurrying in DMF gave the trans quaternary chloride (>98% trans by HPLC).

EXAMPLE 12

Trans-N-3-hydroxypropyl-5'-methoxylaudanosinium chloride (>99% trans by HPLC), 5.06 g, was coupled with, E,E-1,3-phenylenediacryloyl chloride, 1.27 g, by the procedure of Example 4 to yield 6.0 g (100% as trihydrate) of bis{3-[trans-1,2,3,4-tetrahydro-6,7-dimethoxy-N-methyl-1-(3,4,5-trimethoxybenzyl)isoquinolinium]propyl} 1,3-phenylene-(E,E)-diacrylate dichloride.

EXAMPLE 13

5',8-Dimethoxylaudanosine (27.2 g) and 3-iodopropanol (27.2 g) were refluxed in dry acetone (150 mL) for 21 hr. High pressure liquid chromatography (HPLC) showed a cis/trans mixture of 1:4.3. The mixture was stripped to a gum and the excess iodopropanol was extracted with ether. The ether was decanted and the residual gum was dissolved in SD3A (300 mL) with slight warming. Cooling the alcoholic solution at 5° overnight gave a white crystalline solid which was filtered and dried. The yield was 29.2 g (73%) which was assayed as 89.9% of trans-N-3-hydroxypropyl-5',8-dimethoxylaudanosinium iodide and 10.1% of cis-N-3-hydroxypropyl-5',8-dimethoxylaudanosinium iodide. The mixture was recrystallized twice from SD3A (3.4 mL/g) to give 24.4 g (84% recovery) of a mixture assayed by HPLC as 97.8% trans and 2.2% cis iodides, mp 160°–163° C. The mixture was dissolved in aqueous methanol (300 mL) and the solution was passed through a column packed with Dowex 1-X8 ion exchange resin (75 g, Cl$^-$ form). The column was rinsed with methanol (150 mL) and the eluate and washings were combined, stripped to a white solid, triturated with acetone, filtered and dried. The yield was 18.1 g (87%) which was assayed by HPLC as 100% trans.

Calc. for $C_{26}H_{38}NO_7Cl.2H_2O$: C, 56.98; H, 7.72; N, 2.56; Cl, 6.47; Found: C, 56.97; H, 7.74; N, 2.52; Cl, 6.47.

EXAMPLE 14

Trans-N-3-hydroxypropyl-5',8-dimethoxylaudanosinium chloride (2.0 g) was coupled with 1,4-phenylenedipropionyl chloride (0.48 g) by the procedure of Example 4 to yield 700 mg (31% as a tetrahydrate) of bis{3-[trans-1,2,3,4-tetrahydro-6,7,8-trimethoxy-N-methyl-1-(3,4,5-trimethoxybenzyl)isoquinolinium]propyl} 1,4-phenylenedipropionate dichloride.

EXAMPLE 15

According to the procedure of Example 13, laudanosine (34 g) was quaternized with 3-iodopropanol (26 g) to give a 3:1 ratio of trans/cis N-3-hydroxypropyl-laudanosinium iodides. Crystallization of the crude mixture gave the pure trans iodide which was converted to the corresponding pure trans chloride (>99% by HPLC). The yield for the quaternization was 87% and for the anion exchange was 82%.

EXAMPLE 16

Trans-N-3-hydroxypropyllaudanosinium chloride (3.6 g) was coupled with 1,4-phenylenedipropionyl chloride (0.96 g) by the procedure of Example 4 to yield 2.8 g (69% as a tetrahydrate) of bis{3-[trans-1,2,3,4-tetrahydro-6,7-dimethoxy-N-methyl-1-(3,4-dimethoxybenzyl)isoquinolinium]propyl} 1,4-phenylenedipropionate dichloride.

EXAMPLE 17

Trans-N-3-hydroxypropyllaudanosinium chloride (5.0 g) was coupled with E,E-1,4-phenylenediacryloyl chloride (1.35 g) by the procedure of Example 4 to yield 2.3 g (40% as a tetrahydrate) of bis{3-[trans-1,2,3,4-tetrahydro-6,7-dimethoxy-N-methyl-1-(3,4-dimethoxybenzyl)isoquinolinium]propyl} 1,4-phenylene-(E,E)-diacrylate dichloride.

EXAMPLE 18

Trans-N-[3-hydroxypropyl]-5',8-dimethoxylaudanosinium chloride (2.0 g), 1,3-phenylenedipropionic acid (0.34) and p-toluenesulfonic acid monohydrate (0.94) were refluxed in 150 mL dichloroethane in a 500 mL one neck round bottom flask fitted with magnetic spin bar, Soxhlet extractor containing 4A° molecular sieves, reflux condenser and drying tube. After 50 hrs, solvent was stripped at reduced pressure leaving 3.3 g of a gummy residue. The gum was dissolved in 50 mL warm isopropanol. After cooling at 0° C., isopropanol was decanted from an oil which had settled. The oil was dissolved in 100 mL CHCl$_3$ and washed with 100 mL H$_2$O. CHCl$_3$ was stripped and the residue was dissolved in 50 mL warm methyl ethyl ketone. The solution was cooled and solvent was decanted from an oil. The material was lyophilized from CH$_3$OH to give trans,trans-2,2'-(1,3-phenylenebis(ethylenecarbonyloxytrimethylene))-bis(1,2,3,4-tetrahydro-6,7,8-trimethoxy-2-methyl-1-(3,4,5-trimethoxybenzyl)isoquinolinium) ditosylate (also known as bis{3-[trans-1,2,3,4-tetrahydro-6,7,8-trimethoxy-N-methyl-1-(3,4,5-trimethoxybenzyl)isoquinolinium]propyl} 1,3-phenylenedipropionate ditosylate), 0.54 g (24%), 90.6% diester and 9.4% halfester by HPLC. Elemental analysis supports the ditosylate with 3.5 H$_2$O.

Calc. for $0.96(C_{64}H_{86}N_2O_{16}2C_7H_7O_3S) + 0.094(C_{37}H_{50}NO_{10}C_7H_7O_3S)3.5$ H$_2$O: C, 60.52; H, 6.99; N, 1.80; S, 4.12; Cl, 0.0; Found: C 60.50; H, 6.81; N, 1.88; S, 3.50; Cl, 0.0.

EXAMPLE 19

The optically active enantiomers 2,2'-(1,3-phenylenebis(ethylenecarbonyloxytrimethylene))-bis((1R,2S)-1,2,3,4-tetrahydro-6,7,8-trimethoxy-2-methyl-1-(3,4,5-trimethoxybenzyl)isoquinolinium) ditosylate and 2,2'-(1,3-phenylenebis(ethylenecarbonyloxytrimethylene))bis((1S,2R-1,2,3,4-tetrahydro-6,7,8-trimethoxy-2-methyl-1-(3,4,5-trimethoxybenzyl)isoquinolinium) ditosylate are synthesized by first resolution at the 1-position of the 5',8-dimethoxylaudanosine base to its R and S enantiomers. Quaternization of the R base followed by separation of the cis isomer (1R,2R) leads to the pure trans quaternary salt (1R,2S). The optically active trans quaternary salt (1R,2S) is then converted to the optically active diester. By utilizing the S base and proceeding through the same sequence the other enantiomer of the diester is obtained.

Alternatively the trans N-(3-hydroxypropyl)-5',8-dimethoxylaudanosinium salt is resolved using a resolving agent to its enantiomers (1R,2S) and (1S,2R) which are then used to obtain the two enantiomers of the diester.

As used herein R and S denote chirality according to the Cahn-Ingold-Prelog system [Angew. Chem. Int. Ed. Engl., 5, 385 (1966) and Pure Appl. Chem., 45, 13 (1976)].

The RS, RS and SR, SR compounds are important because of their short-acting properties.

Short acting as used herein is defined as having a duration of action of about 20 minutes or less.

Pharmacological Activity

Cynomolgus monkeys were anaesthetized with thiopental (35–40 mg/kg) and diazepam (2—3 mg/kg) given intramuscularly. Anaesthesia was maintained with a mixture of halothane (0.25–0.75%), nitrous oxide (60%) and oxygen (40%).

Bis{3-[trans-1,2,3,4-tetrahydro-6,7-dimethoxy-N-methyl-1-(3,4,5-trimethoxybenzyl)isoquinolinium]propyl} 1,3-phenylenedipropionate dichloride (compound A), bis{3-[1,2,3,4-tetrahydro-6,7-dimethoxy-N-methyl-1-(3,4,5-trimethoxybenzyl)isoquinolinium]propyl} 1,3-phenylenedipropionate diiodide (mixture of cis and trans isomers, Compound B) or bis{3-[cis-1,2,3,4-tetrahydro-6,7-dimethoxy-N-methyl-1-(3,4,5-trimethoxybenzyl)isoquinolinium]propyl} 1,3-phenylenedipropionate diiodide (Compound C) was administered intravenously. The common peroneal nerve was stimulated supramaximally with square wave pulses of 0.2 m sec duration at a rate of 0.15 Hz. Twitch contractions were recorded via the tendon of the tibialis anterior muscle.

The ED$_{95}$, i.e. the dose required to produce 95% block of the twitch response, of compound A was 0.4–0.6 mg/kg and that of compound B was 0.5–1.0 mg/kg and that of compound C was 0.8–1.1 mg/kg (expressed as mg/kg cation).

We claim:

1. A method for the preparation of a pharmacuetically acceptable salt of 2,2'-(1,3-phenylenebis(ethylenecarbonyloxytrimethylene)bis(IR,2S)-1,2,3,4-tetrahydro-6,7,8-trimethoxy-2-methyl-1-(3,4,5-trimethoxybenzyl)isoquinolinium cation or 2,2'-(1,3-phenylenebis(ethylenecarbonyloxytrimethylene)-bis(1S,2R)-1,2,3,4-tetrahydro-6,7,8-trimethoxy-2-methyl-1-(3,4,5-trimethoxybenzyl)isoquinolinium cation which comprises:

(1) the resolution of the R or S isomer of 5',8-dimethoxylaudanosine base from a mixture of the R and S isomers;

(2) addition of a 3-hydroxypropyl halide to the separated R or S isomer to form the corresponding optically active N-(3-hydroxypropyl)tetrahydroisoquinolinium salt (cis, trans mixture);

(3) separation by crystalization of the trans isomer from the cis, trans mixture; and (4) condensing the trans isomer with an appropriate 1,3-phenylenedipropionic acid.

* * * * *